United States Patent
Pinhack

(10) Patent No.: US 9,588,070 B2
(45) Date of Patent: Mar. 7, 2017

(54) COMBUSTION CALORIMETER WITH A DECOMPOSITION VESSEL

(75) Inventor: Hubert Pinhack, Bad Krozingen (DE)

(73) Assignee: IKA—Werke GmbH & Co. KG, Staufen (DE)

( * ) Notice: Subject to any disclaimer, the term of this patent is extended or adjusted under 35 U.S.C. 154(b) by 600 days.

(21) Appl. No.: 14/115,699

(22) PCT Filed: Apr. 19, 2012

(86) PCT No.: PCT/EP2012/001704
§ 371 (c)(1),
(2), (4) Date: Nov. 5, 2013

(87) PCT Pub. No.: WO2012/156017
PCT Pub. Date: Nov. 22, 2012

(65) Prior Publication Data
US 2014/0079090 A1     Mar. 20, 2014

(30) Foreign Application Priority Data
May 17, 2011   (DE) .......... 10 2011 101 733

(51) Int. Cl.
G01N 25/42     (2006.01)
G01N 25/22     (2006.01)
G01N 25/26     (2006.01)

(52) U.S. Cl.
CPC ........... *G01N 25/22* (2013.01); *G01N 25/26* (2013.01)

(58) Field of Classification Search
USPC .................................. 374/31–41
See application file for complete search history.

(56) References Cited

U.S. PATENT DOCUMENTS

| 4,616,938 A * | 10/1986 | Bonnard | G01N 25/40 374/38 |
| 5,547,282 A * | 8/1996 | Pinhack | G01K 17/00 374/33 |
| 6,627,451 B2 | 9/2003 | Pinhack et al. | |
| 2010/0316087 A1* | 12/2010 | Pinhack | G01N 25/26 374/33 |
| 2011/0069804 A1* | 3/2011 | Lynch | G21C 13/032 376/372 |

FOREIGN PATENT DOCUMENTS

| DE | 3221548 | 12/1983 |
| DE | 3520529 | 12/1986 |
| DE | 19542138 | 10/1996 |
| EP | DE29 24 477 | 1/1981 |

* cited by examiner

*Primary Examiner* — Lisa Caputo
*Assistant Examiner* — Nasir U Ahmed
(74) *Attorney, Agent, or Firm* — Gordon & Jacobson, P.C.

(57) ABSTRACT

A combustion calorimeter (1) has a housing (6) and therein a detachably mounted decomposition vessel (2) with sample holder (11) and ignition apparatus (12) in its reaction chamber (3). The wall (4) of the decomposition vessel (2) and also the upper decomposition wall (5) here have in the vertical use position a wall thickness that increases from the bottom to the top in order to conduct the heat generated in a combustion process if possible into the upper region of the decomposition vessel (2), where also at least one temperature sensor (7) can be arranged. Owing to the increase in thickness of the delimitation of the internal or reaction space (3), the heat can be distributed therein more favorably.

16 Claims, 1 Drawing Sheet

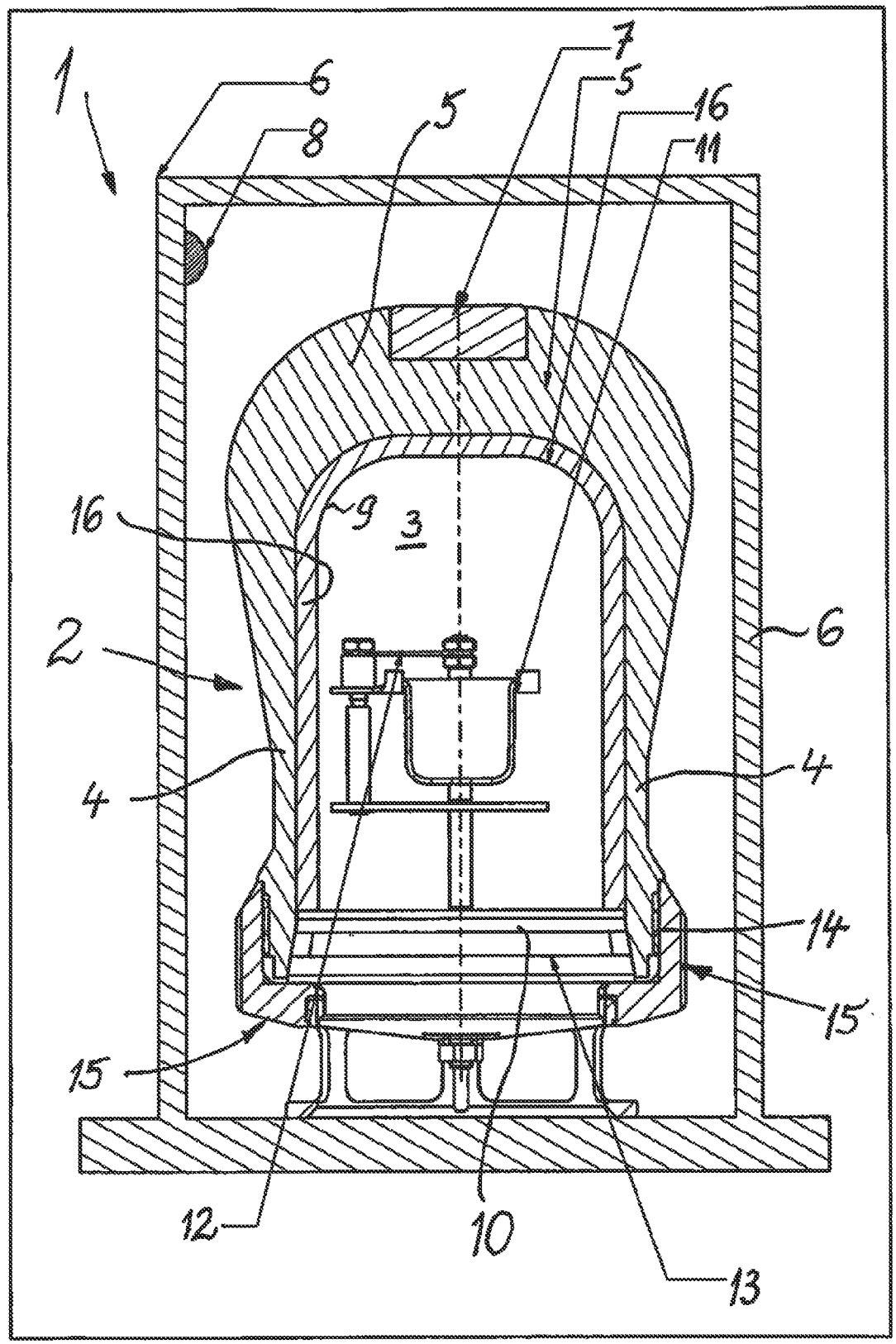

COMBUSTION CALORIMETER WITH A DECOMPOSITION VESSEL

CROSS-REFERENCE TO RELATED APPLICATIONS

This application claims priority from PCT/EP2012/001704, filed Apr. 19, 2012, which claims priority from DE 10 2011 101 733.3, filed May 17, 2011, which are hereby incorporated by reference herein in their entireties.

BACKGROUND OF THE INVENTION

The invention relates to a combustion calorimeter comprising a decomposition vessel, the interior space of which is designed in particular as a cylindrical reaction chamber by way of side walls and a top sealing wall and can be tightly sealed, wherein the decomposition vessel is replaceably arranged in a housing and comprises at least one temperature sensor for measuring the temperature of the decomposition vessel, wherein at least one second temperature sensor is located on the inside of the wall region of the housing, and wherein the decomposition vessel is located in a substantially vertical orientation in the housing in the usage position.

Such a combustion calorimeter comprising a decomposition vessel is known from DE 43 14 454 C1 and has been tried and tested.

So as to be able to measure the heat generated by a combustion process, one or more temperature sensors are required in the decomposition vessel. The problem here is that the absorbed heat is to be determined as precisely as possible, or as accurately as possible, which is done by way of the increase in the temperature of the decomposition vessel.

Because such decomposition vessels generally require a cover having a device for holding the sample vessel so as to be charged from above, as is known from DE 195 42 138 C1, for example, transition obstacles result on threads or on material changes and the like, notably in the top region of such a decomposition vessel where the heat predominantly migrates to after the decomposition process, whereby the heat flow may be delayed. This may make the accuracy of determining the heat that developed more difficult, or even impossible. Both the progression over time and the actual value of the heat that developed can be imprecise or fluctuate due to such obstructions.

SUMMARY OF THE INVENTION

It is therefore the object to create a calorimeter of the type defined above, comprising a decomposition vessel that allows greater accuracy in determining the heat that developed.

So as to achieve this object, the calorimeter described above is characterized in that the decomposition vessel has a greater wall thickness in the region that is at the top in the usage position than in the bottom region thereof, the wall thickness of the delimitation of the decomposition vessel increases from the bottom to the top up to the region of the greatest wall thickness, and the increase in the wall thickness is steady and provided to be rectilinear, or curved in a convex shape, or curved in a concave shape, in the longitudinal section.

In this way, the heat rising to the top substantially on its own is absorbed accordingly well and almost entirely in the top region having the greater wall thickness, so that fast, and also accurate, measurement of this heat by way of the increase in the temperature is possible. The reason for this is that, due to the greater wall thickness, the higher thermal capacity of the composition vessel is located in this top region. For uniform conveyance of the heat into the region having the greater wall thickness, it is favorable for the increase in the wall thickness to be steady, which is to say not to be stepped or sudden. It is advantageous for good propagation and conduction of the heat, with good measurability at the same time, if the cross-section of the decomposition vessel is circular both in the bottom region and in the top region thereof, on the inside as well as on the outside. All wall regions thus have the same distance from a central heat source and can be heated accordingly uniformly.

According to a particularly expedient embodiment of the invention that is essential, the upper sealing wall may be included in the increase in the wall thickness of the side walls, and the at least one temperature sensor may be arranged and inserted in this top sealing wall forming a thickened wall section as compared to the side walls. As a result, the effect of the heat rising to the top in a region having higher thermal capacity is continued into the top sealing wall, where expediently a temperature sensor can be accommodated well.

It is advantageous for this purpose if the temperature sensor is arranged and inserted in the center of the top sealing wall designed as a thickened wall section.

The increase in the wall thickness from the bottom to the top up to the top sealing wall may be selected so that heating is the same both in the bottom lower-lying region having a thinner wall thickness and in the top region having a thicker wall thickness. Optionally, it may be determined by way of experimentation how to design the wall thickness so that, with respect to the rising heat, the top and bottom regions of the decomposition vessel are still uniformly heated.

The outer contour of the decomposition vessel can be designed to be approximately conical or drop-shaped, with the cross-section increasing from the bottom to the top. This yields the desired substantially uniform heating with increasing wall thickness.

The cross-section of the inner cavity of the decomposition vessel can be reduced in the top region by an inside rounded region or tapered region or can be curved on the inside analogously to the curved outer contour. It can thus be achieved that the wall thickness is also substantially uniformly thick in this top region or that the thickness thereof at the transitions can also increase uniformly.

The temperature sensor, or the temperature sensors arranged in the wall of the decomposition vessel, can be arranged or inserted in the top region of the decomposition vessel in a thickened wall section, in particular in the center of the top sealing wall of the decomposition vessel. First, temperature sensors can be accommodated well in a thickened wall section, and secondly the majority of the heat also rises in this thickened region.

A modified embodiment of the invention may provide for the top wall region and/or the top sealing wall of the decomposition vessel to be subsequently connected, in particular detachably or non-detachably, to the lower-lying region or regions of the side wall. This is favorable in terms of producing this decomposition vessel in the shape thereof having an increasing wall thickness.

According to a further embodiment, the top wall region of the decomposition vessel which is detachably connected to the lower-lying wall regions may be replaceable, in particular replaceable with a section having different thermal capacity. The thermal capacity of the decomposition vessel can thus be modified or adapted to different needs. The replaceable part could have a greater mass or a different material, or both, if the thermal capacity needed to be increased. Conversely, the thermal capacity can be reduced, for example if the calorific value determination of a substance showed that the combustion thereof will generate only little heat.

The bottom wall region of the decomposition vessel can surround the access opening for a sample holder and for sample charging and can be detachably attached to a mounting arranged in the housing using a screw closure or bayonet catch. The decomposition vessel can thus be easily detached from the usage position thereof and a sample holder can then be appropriate charged. This holder can optionally be installed in the housing, so that the decomposition container can be placed over it and then fastened thereon.

The decomposition vessel can be produced from a material having high specific thermal capacity, preferably aluminum or an aluminum alloy and/or copper or a copper alloy, and can comprise a lining made of high-alloy steel or chromium nickel steel, for example, in particular on the inside. As a result of such a lining, the advantages known from DE 195 42 138 01 for the aforementioned materials could be achieved.

Especially when combining individual or several of the features and measures described above, a combustion calorimeter comprising a decomposition vessel is achieved, with the aid of which the heat that developed during a combustion process and was absorbed by the decomposition vessel can be determined as accurately as possible, in particular if a dry or waterless calorimeter is involved.

An exemplary embodiment of the invention will be described hereafter in greater detail based on the drawing.

BRIEF DESCRIPTION OF THE DRAWING

The only FIGURE shows a longitudinal sectional view of a combustion calorimeter according to the invention, comprising a decomposition vessel in a housing.

DETAILED DESCRIPTION OF THE PREFERRED EMBODIMENTS

A combustion calorimeter of the type and having the mode of operation disclosed in DE 43 14 454 C1, denoted in the overall by reference numeral 1, comprises a decomposition vessel, which in the overall is denoted by reference numeral 2 and the interior space 3 of which is designed as a substantially cylindrical reaction chamber by way of side walls 4 and a top sealing wall 5 and is tightly sealed in the usage position.

The decomposition vessel 2 is replaceably arranged in a housing 6 and comprises a temperature sensor 7 for measuring the temperature 7 of the decomposition vessel 2.

On the inside of the wall region of the housing 6, at least one second temperature sensor 8 is apparent, which can be connected, for example, to a temperature control device for the decomposition vessel and/or to a computing or control device, which is not shown in detail.

In the usage position, the longitudinal center axis of the decomposition vessel 2 is oriented vertically in the housing 6, which likewise corresponds to the configuration according to DE 43 14 454 C1.

It is clearly apparent in the drawing that the decomposition vessel 2 has a greater wall thickness in the region that is at the top in the usage position than in the lower region thereof, wherein the wall thickness of the decomposition vessel 2 increases from the bottom to the top up to the region having the greatest wall thickness. The increase in the wall thickness is steady and rectilinear in the longitudinal section, which is to say the jacket lines of the outside of the decomposition vessel 2 extend from a thinnest point of the wall 4 upward in a rectilinear oblique manner and thereby result in a steadily increasing wall thickness, as is easily apparent from the figure.

The cross-section of the decomposition vessel 2 is circular both in the bottom region and in the top region thereof, on the inside as well as on the outside, so that the increase in the wall thickness is also uniform and evenly large on the circumference in each direction.

The increase in the wall thickness from the bottom to the top up to the top sealing wall 5, and including the same in the increase in the wall thickness, is selected such that heating is the same, or substantially the same, both in the bottom lower-lying region having a thinner wall thickness and in the top region having a thicker wall thickness. The increase in the wall thickness in the vertical regions and the shape of the outside on the top sealing wall 5 are selected for this purpose so that the decomposition vessel 2 has an approximately drop-shaped design, wherein in the usage position the cross-section of this "drop" increases from the bottom to the top. The interior space 3 of the decomposition vessel 2 has a reduced cross-section in the top region due to a rounded region 9 on the inside, which could also be designed as a tapered region, and is curved on the inside in some regions analogously to the curved outer contour in keeping with this rounded region 9. This contributes to a steady increase in the magnitude of the wall thickness from the side to the top, where then again a uniform magnitude of the wall thickness is provided for a certain central region.

The drawing also indicates that the temperature sensor 7 arranged in the wall of the decomposition vessel 2 is arranged and inserted into a thickened wall section in the top region of the decomposition 2, which here is the center of the top sealing wall 5, to which point the heat flows from the surrounding side wall 4 toward the top. It is also possible to arrange multiple temperature sensors 7 in the body or the wall region of the decomposition vessel 2 so as to optionally be able to measure and observe multiple temperatures.

It is apparent from the drawing that the temperature sensor 7 extends approximately over the region of the top sealing wall 5, the region also extending in an approximately rectilinear manner horizontally in terms of the shape of the interior space 3.

In the exemplary embodiment, the side wall 4 and the top sealing wall 5 of the decomposition vessel 2 are integrally connected, which allows a steady and substantially undisturbed heat flow. From a manufacturing point of view, however, a multi-part design would also be conceivable, in which the two wall sections 4 and 5 could subsequently be connected to each other in a suitable location either detachably, for example by way of a thread, or non-detachably.

The access opening 10 for a sample holder 11 having an ignition device, and thus also for charging the sample, is provided in the bottom wall region at the bottom end of the side wall 4 of the decomposition vessel 2 and is surrounded by the bottom region of the side wall 4. This opening 10 can be closed by a cover 13 in the usage position. The entire system can be detachably attached to a mounting 15 arranged in the housing 6 in the bottom region by way of a screw closure or bayonet catch 14 and in the usage position is attached in accordance with the drawing.

It is also apparent from the drawing that the decomposition vessel 2 has a lining 16 on the inside, for example made of high-alloy steel or chromium nickel steel. It is thus possible to produce the decomposition vessel itself from an optionally heat-sensitive metal or an alloy, such as aluminum or an aluminum alloy, or copper or a copper alloy, or optionally even from titanium.

The combustion calorimeter 1 comprises a housing 6 and a decomposition vessel 2 detachably installed therein, the vessel having a sample holder 11 and an ignition device 12 in the reaction chamber 3 thereof. The wall 4 of the decomposition vessel 2, and also the top sealing wall 5, have an increasing wall thickness from the bottom to the top in the vertical usage position, so as to conduct the heat generated during a combustion process to the extent possible into the top region of the decomposition vessel 2, where at least one temperature sensor 7 can also be arranged. As a result of the increase in the thickness of the delimitation of the interior space or reaction chamber 3, the heat can be distributed more favorably therein.

The invention claimed is:

1. A combustion calorimeter (1) comprising a housing and a decomposition vessel (2) within the housing, the interior space (3) of the decomposition vessel designed as a cylindrical reaction chamber by way of side walls and an upper sealing wall (5), and a mounting to which the side walls of the reaction chamber are adapted to be tightly sealed, the decomposition vessel (2) being replaceably arranged in the housing and comprising at least one temperature sensor (7) for measuring the temperature of the decomposition vessel (2), at least one second temperature sensor (8) being located on the inside of a wall region of the housing (6), and the decomposition vessel (2) being in an upright orientation in the housing (6) in a usage position, characterized in that the decomposition vessel (2) has a greater wall thickness in a region that is at the top in the usage position than in the lower region thereof, the wall thickness of the decomposition vessel (2) increases from the bottom to the top up to the region having the greatest wall thickness, and the increase in the wall thickness is steady and provided to be rectilinear, or curved in a convex shape, or curved in a concave shape, in the longitudinal section.

2. The combustion calorimeter (1) according to claim 1, characterized in that the top sealing wall (5) is included in the increase in the wall thickness of the side walls (4), and the at least one temperature sensor (7) is arranged and inserted in this top sealing wall (5) forming a thickened wall section as compared to the side walls (4).

3. The combustion calorimeter according to claim 1, characterized in that the temperature sensor (7) is arranged and inserted in the center of the top sealing wall (5) designed as a thickened wall section.

4. The calorimeter according to claim 1, further characterized in that the cross-section of the decomposition vessel (2) is circular both in the bottom region and in the top region thereof, on the inside as well as on the outside.

5. A calorimeter according to claim 1, characterized in that the increase in the wall thickness from the bottom to the top up to, and including, the top sealing wall (5), is selected so that heating is the same both in the bottom lower-lying region having a thinner wall thickness and in the top region having a thicker wall thickness.

6. A calorimeter according to claim 1, characterized in that the outer contour of the decomposition vessel (2) is approximately conical or drop-shaped, the cross-section increasing from the bottom to the top.

7. A calorimeter according to claim 1, characterized in that the cross-section of the interior space (3) of the decomposition vessel (2) is reduced in the top region by a rounded region (9) or a tapered region, or is curved on the inside analogously to the curved outer contour.

8. A calorimeter according to claim 1, characterized in that the at least one temperature sensor arranged in the wall of the decomposition vessel (2) is or are arranged or inserted in the top region of the decomposition vessel (2) in a thickened wall section in a center of the top sealing wall of the decomposition vessel.

9. A calorimeter according to claim 1, characterized in that at least one of the top wall region and the top sealing wall (5) of the decomposition vessel (2) are subsequently connected to the lower-lying regions of the side wall (4).

10. A calorimeter according to claim 1, characterized in that the top wall region of the decomposition vessel (2) which is detachably connected to the lower-lying wall regions is replaceable with a section having different thermal capacity.

11. A calorimeter according to claim 1, characterized in that the bottom wall region (4) of the decomposition vessel (2) surrounds the access opening (10) for a sample holder and for sample charging and can be detachably attached to a mounting (15) arranged in the housing (6) by way of one of a screw closure and bayonet catch.

12. A calorimeter according to claim 1, characterized in that the decomposition vessel (2) is produced from a material having high specific thermal capacity and comprises a lining (16) made of one of high-alloy steel and chromium nickel steel on the inside thereof.

13. A calorimeter according to claim 1, characterized in that the at least one temperature sensor in intimate contact with the decomposition vessel.

14. A calorimeter according to claim 1, characterized in that the at least one temperature sensor is located at a top region of the decomposition vessel.

15. A calorimeter according to claim 1, characterized in that the at least one temperature sensor is located in a wall of the decomposition vessel.

16. A calorimeter according to claim 1, characterized in that the at least one temperature sensor is located on or in the region of the decomposition vessel having the greater wall thickness.

* * * * *